(12) United States Patent
Bobba Venkata et al.

(10) Patent No.: US 9,255,105 B2
(45) Date of Patent: Feb. 9, 2016

(54) PROCESS OF PREPARING ALCAFTADINE

(71) Applicant: Enaltec Labs Pvt. Ltd., Navi Mumbai (IN)

(72) Inventors: Sivakumar Bobba Venkata, Maharashtra (IN); Eswara Rao Kodali, Maharashtra (IN); Girish Bansilal Patel, Maharashtra (IN); Sanjay Dashrath Vaidya, Maharashtra (IN); Alok Pramod Tripathi, Maharashtra (IN)

(73) Assignee: ENALTEC LABS PRIVATE LIMITED, Navi Mumbai (IN)

( * ) Notice: Subject to any disclaimer, the term of this patent is extended or adjusted under 35 U.S.C. 154(b) by 0 days.

(21) Appl. No.: 14/391,465

(22) PCT Filed: Nov. 19, 2013

(86) PCT No.: PCT/IB2013/002585
§ 371 (c)(1),
(2) Date: Oct. 9, 2014

(87) PCT Pub. No.: WO2014/087208
PCT Pub. Date: Jun. 12, 2014

(65) Prior Publication Data
US 2015/0119570 A1    Apr. 30, 2015

(30) Foreign Application Priority Data

Dec. 6, 2012  (IN) .......................... 3449/MUM/2012
Dec. 6, 2012  (IN) .......................... 3450/MUM/2012

(51) Int. Cl.
*C07D 487/04*    (2006.01)

(52) U.S. Cl.
CPC ................................... *C07D 487/04* (2013.01)

(58) Field of Classification Search
CPC ..................................................... C07D 487/04
USPC ........................................................ 540/579
See application file for complete search history.

(56) References Cited

FOREIGN PATENT DOCUMENTS

WO         92/22551 A1     12/1992
WO       2014/083571 A1     6/2014

OTHER PUBLICATIONS

Mohrig et al., Technique 9: Recrystallization, Techniques in Organic Chemistry, Second Edition, pp. 100-104 (2006).*

* cited by examiner

*Primary Examiner* — Deepak Rao
(74) *Attorney, Agent, or Firm* — Bruzga & Associates; Charles E. Bruzga; Jay S. Pattumudi

(57) ABSTRACT

The present invention is related to a substantially pure compound of structural formula (VIII), a process for the purification of a compound of structural formula (VIII) and an improved process of preparing an alcaftadine compound of structural formula (I).

6 Claims, 2 Drawing Sheets

PROCESS OF PREPARING ALCAFTADINE

FIELD OF THE INVENTION

The field relates to an improved process of preparing substantially pure alcaftadine comprising reacting compound of structural formula VIII with more than 20 moles of oxidizing reagent in an organic solvent to obtain alcaftadine. The field also relates to a process of preparing alcaftadine compound of structural formula I by employing a substantially pure compound of structural formula VIII.

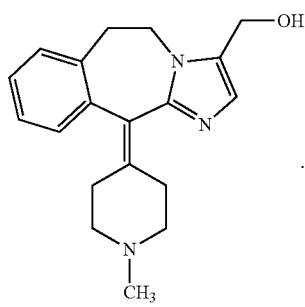

Formula VIII

BACKGROUND OF THE INVENTION

Alcaftadine is chemically 6,11-dihydro-11-(1-methyl-4-piperidinylidene)-5H-imidazo[2,1-b][3]benzazepine-3-carboxaldehyde and is known from U.S. Pat. No. 5,468,743 and is represented by a compound of structural formula I:

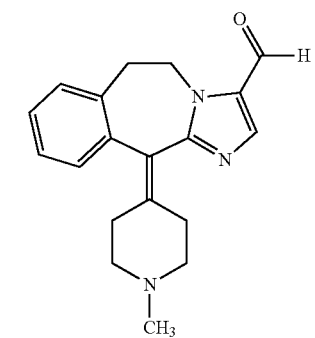

Formula I

Alcaftadine is a $H_1$ histamine receptor antagonist sold in USA under the proprietary name of "LASTACAFT" and is indicated for the prevention of itching associated with allergic conjunctivitis.

U.S. Pat. No. 5,468,743 describes analogous processes of preparing alcaftadine compound of structural formula I as shown below in scheme no. I, scheme no. II and scheme no. III:

Scheme I

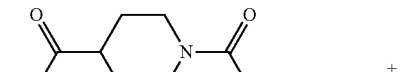

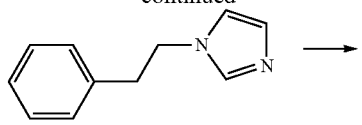

Formula III

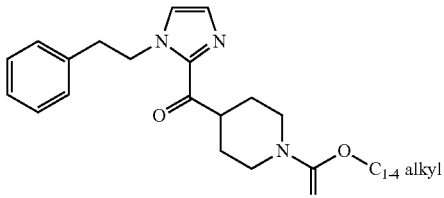

Formula IV

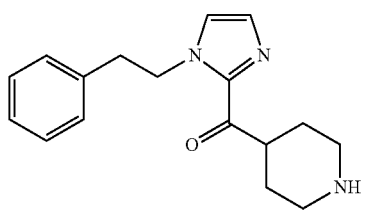

Formula V

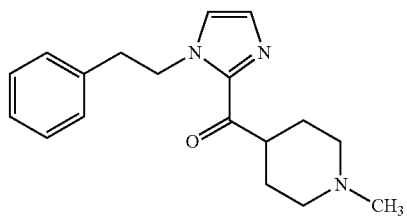

Formula VI

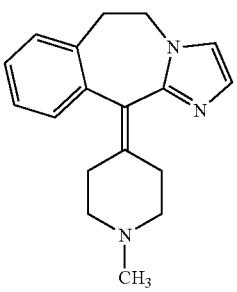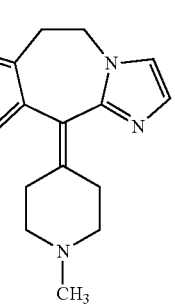

Formula VII

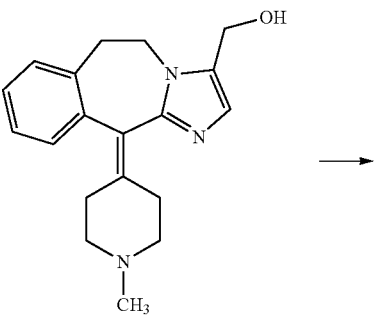

Formula VIII

3
-continued
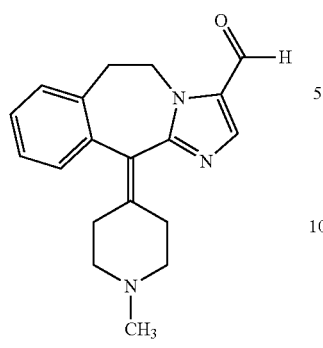
Formula I
4
-continued
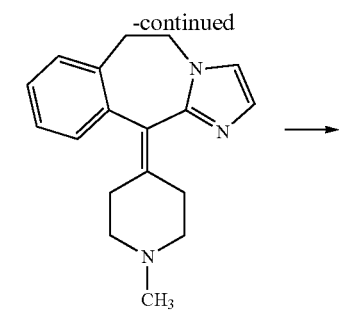
Formula VII
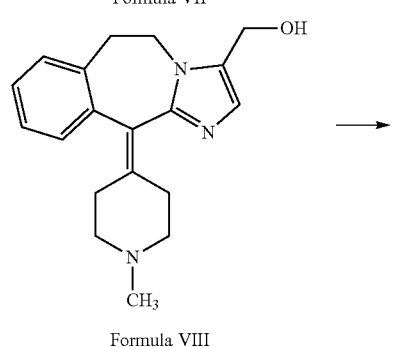
Formula VIII
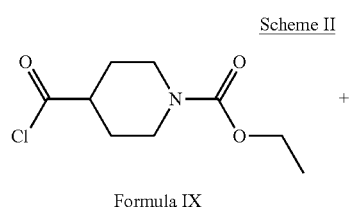
Formula I
Scheme II
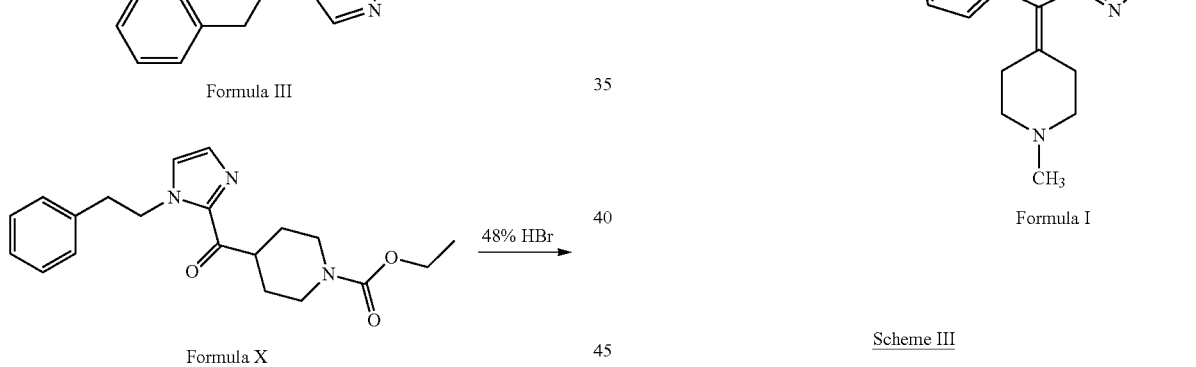
Scheme III
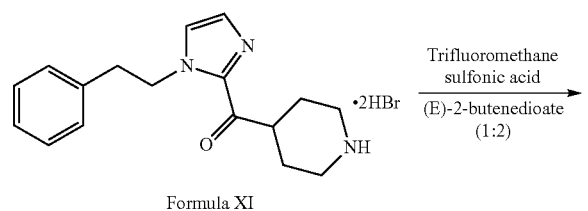
Formula XIII
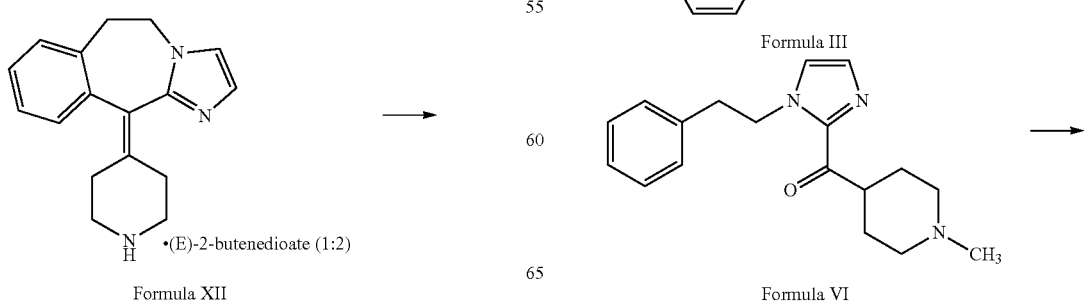
Formula VI

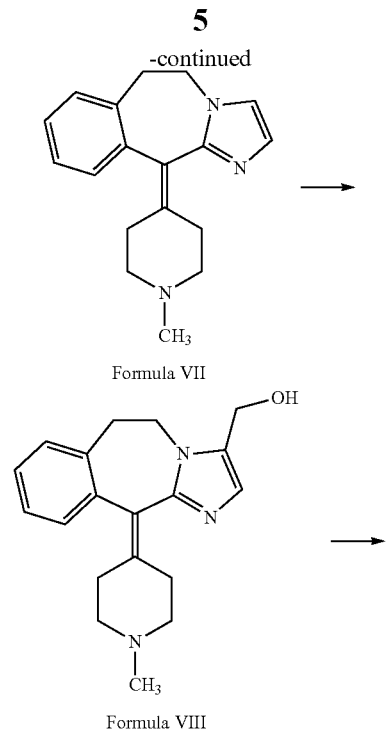

Formula VII

Formula VIII

The processes of preparing compound of structural formula VIII according to the above mentioned references produce more than 25% of compound of structural formula XIV:

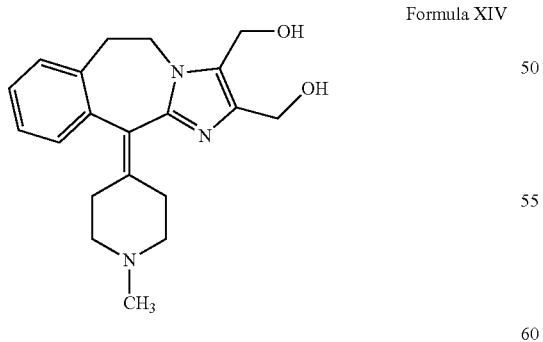

Formula XIV

The compound of structural formula XIV is carry-forwarded into the further steps of reactions of preparing alcaftadine compound of structural formula I and therefore there is a need in the art to develop an improved process of preparing compound of structural formula VIII, which obviates the prior-art problems.

Further, the prior art processes for preparing alcaftadine compound of structural formula I comprises treating compound of structural formula VIII with less than 20 moles of oxidizing reagent which leads to incomplete reaction and causes low yield of alcaftadine.

Accordingly, there is a need in the art to develop an improved process of preparing alcaftadine compound of structural formula I, which obviates the prior-art problems.

The inventors of the present invention have developed an improved process for the preparation of alcaftadine using substantially pure compound or purified compound of structural formula VIII, resulting in higher yield of alcaftadine. The improved process is cost effective and has fewer steps as compared to the process disclosed in the prior publications.

Further, the inventors have found that treating compound of structural formula VIII with more than 20 moles of oxidizing reagent leads to completion of reaction and results in higher yield of alcaftadine.

SUMMARY OF THE INVENTION

A first aspect of the present invention is to provide a substantially pure compound of structural formula VIII:

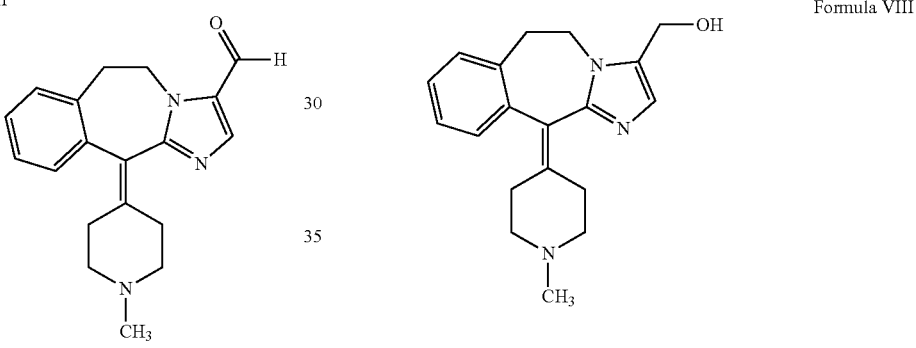

Formula VIII

According to another aspect, the present invention relates to a process for the purification of compound of structural formula VIII.

According to another aspect, the present invention relates to a process of purification of compound of structural formula VIII comprising the steps of:
a. dissolving a crude compound of structural formula VIII in tetrahydrofuran solvent, the crude compound having more than 15% of a compound of structural formula XIV; and
b. isolating a substantially pure compound of structural formula VIII having the formula:

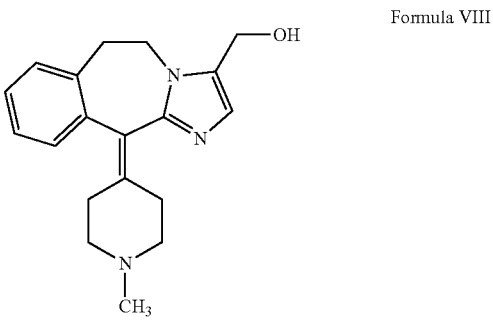 [SMILES: CN1CCC(=C2c3ccccc3CCn3c(CO)cnc32)CC1]

Formula VIII wherein the compound of structural formula XIV has the formula:

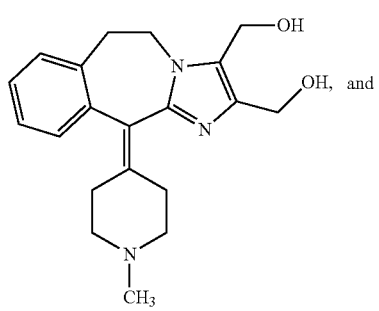

Formula XIV the substantially pure compound of structural formula VIII has less than 15% of a compound of structural formula XIV.

According to another aspect, the present invention relates to a process of preparing alcaftadine compound of structural formula I comprising the steps of:
a. dissolving crude compound of structural formula VIII in tetrahydrofuran solvent;
b. isolating substantially pure compound of structural formula VIII; and
c. converting the substantially pure compound of structural formula VIII into an alcaftadine compound of structural formula I having the formula:

Formula I the crude compound of structural formula VIII has more than 15% of a compound of structural formula XIV and has the formula:

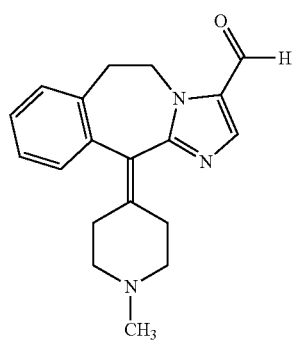

Formula VIII the compound of structural formula XIV has the formula:

Formula XIV

According to another aspect, the present invention relates to solvated compound of structural formula XV:

Formula XV

Solvate

According to another aspect, the present invention relates to tetrahydrofuran solvated compound of structural formula XVI:

Formula XVI

·Tetrahydrofuran solvate

According to another aspect, the present invention relates to a crystalline compound of structural formula VIII.

Another aspect of the present invention is to provide an improved process of preparing an alcaftadine compound of structural formula I.

Another aspect of the present invention is to provide an improved process of preparing alcaftadine comprising reacting a compound of structural formula VIII with more than 20 moles of oxidizing reagent in an organic solvent to obtain an alcaftadine compound of structural formula I:

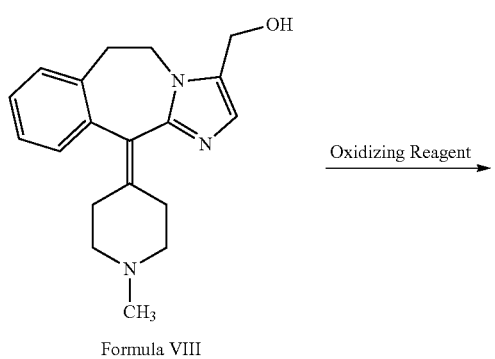

Formula VIII

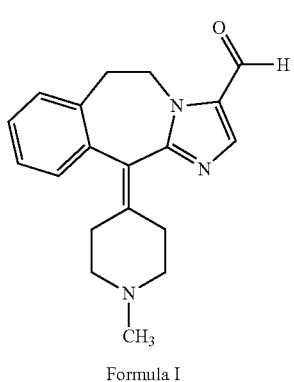

Formula I

Another aspect of the present invention is to provide a substantially compound pure alcaftadine of structural formula I.

Another aspect of the present invention is to provide a process of preparing, substantially pure alcaftadine compound of structural formula I comprising reacting a compound of structural formula VIII with more than 20 moles of oxidizing reagent in an organic solvent to obtain substantially pure alcaftadine compound of structural formula I.

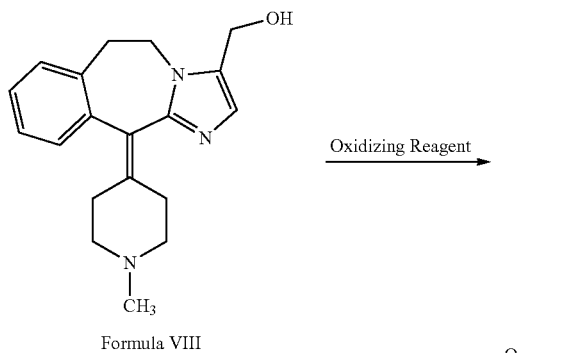

Formula VIII

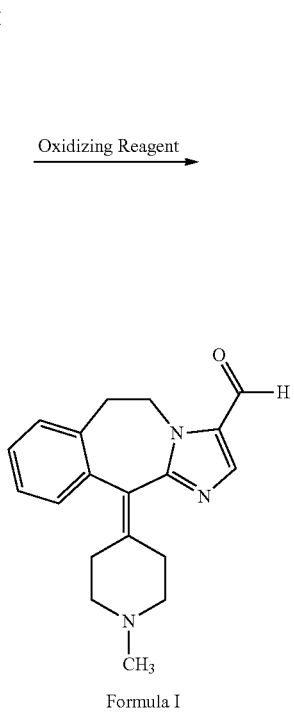

Formula I

BRIEF DESCRIPTION OF THE DRAWINGS

Further features and advantages of the invention will become apparent from reading the following detailed description in conjunction with the following drawings, in which like reference numbers refer to like parts.

DETAILED DESCRIPTION OF THE INVENTION

Figure 1:
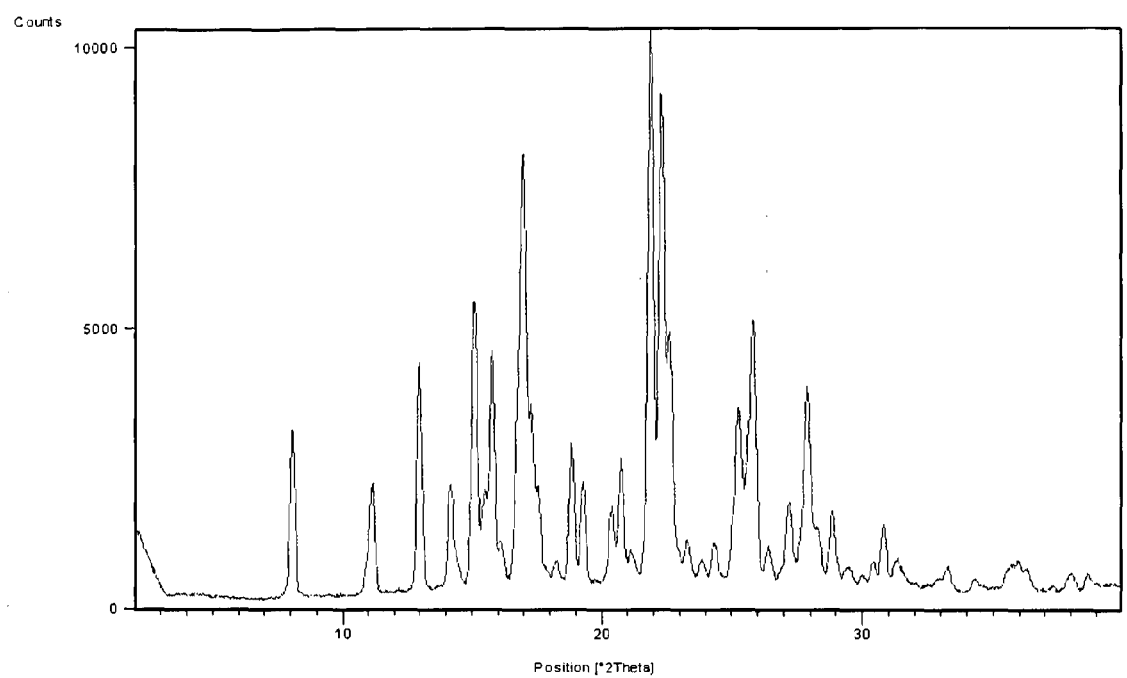
FIG. 1 depicts an X-ray diffraction pattern of a crystalline compound of structural formula VIII.

The examples and the referenced drawings provided in this detailed description are merely exemplary, and should not be used to limit the scope of the claims in any claim construction or interpretation.

In an embodiment, the present invention relates to a process for the preparation of a substantially pure compound of structural formula VIII:

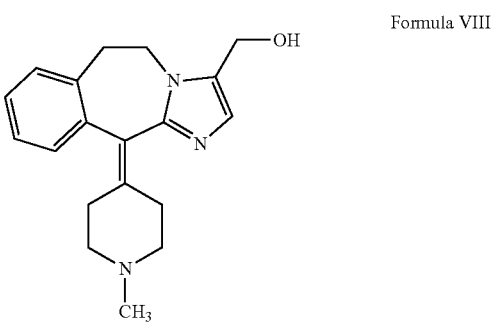 [SMILES: CN1CCC(=C2c3ccccc3CCn3c(CO)cnc32)CC1]

Formula VIII

The term "substantially pure compound of structural formula VIII" described herein refers to a compound of structural formula VIII having less than 15% of compound of structural formula XIV:

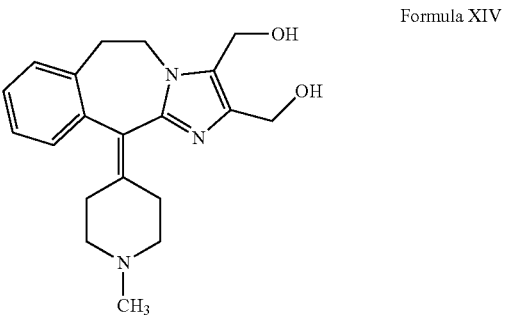 [SMILES: CN1CCC(=C2c3ccccc3CCn3c2nc(CO)c3CO)CC1]

Formula XIV

In another embodiment, the present invention relates to a process for purification of a compound of structural formula VIII comprising the steps of:
  a. dissolving a crude compound of structural formula VIII in an ether solvent and,
  b. isolating a substantially pure compound of structural formula VIII.

The crude compound of structural formula VIII used according to the present invention can be prepared by methods disclosed in the art such as those described in U.S. Pat. No. 5,468,743, the disclosure of which is incorporated herein by reference.

In one preferred embodiment, the purification of a compound of structural formula VIII is carried out by dissolving a crude compound of structural formula VIII in an ether solvent at a temperature in the range of 40° C. to 80° C. and maintained for 30 minutes to 2 hours. The resulting solution was cooled in the range of 20° C. to 30° C. to obtain a pure compound of structural formula VIII.

Ether solvents can be selected from the group comprising, but not limited to, tetrahydrofuran, 1,4-dioxane, diethyl ether, diisopropyl ether, dibutyl ether, methyl tertiary butyl ether, methyl ethyl ether, methyl isobutyl ether or mixture(s) thereof.

The substantially pure compound of structural formula VIII may be isolated by any known process in the at such as filtration, centrifugation, washing, drying or the combinations thereof.

The isolated pure compound of structural formula VIII may be dried at a temperature in the range of 40° C. to 80° C. for a period of 2 horns to 12 hours under reduced pressure.

The solvates of compound of structural formula XV can be selected from the group comprising, but not limited to, tetrahydrofuran solvate, 1,4-dioxane solvate, diethyl ether solvate, diisopropyl ether solvate, dibutyl ether solvate, methyl tertiary butyl ether solvate, methyl ethyl ether solvate or methyl isobutyl ether solvate.

One example of a solvated a compound of structural formula XV includes a tetrahydrofuran solvated compound of structural formula XVI:

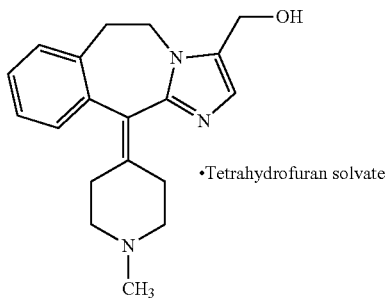

Formula XVI

·Tetrahydrofuran solvate

The isolated substantially pure compound of structural formula VIII may be crystalline or amorphous in nature.

In another embodiment, the present invention relates to a crystalline compound of structural formula VIII characterized by X-ray diffraction pattern having peaks at 8.0, 11.0, 12.8, 14.0, 15.0, 15.7, 16.9, 18.7, 19.3, 20.3, 20.6, 21.8, 22.2, 22.6, 25.2, 25.8, 27.1, 27.8, 28.8, 30.7±0.2 degrees two theta.

In another embodiment, the present invention relates to a crystalline compound of structural formula VIII characterized by X-ray diffraction pattern as depicted in FIG. 1.

Figure 2:
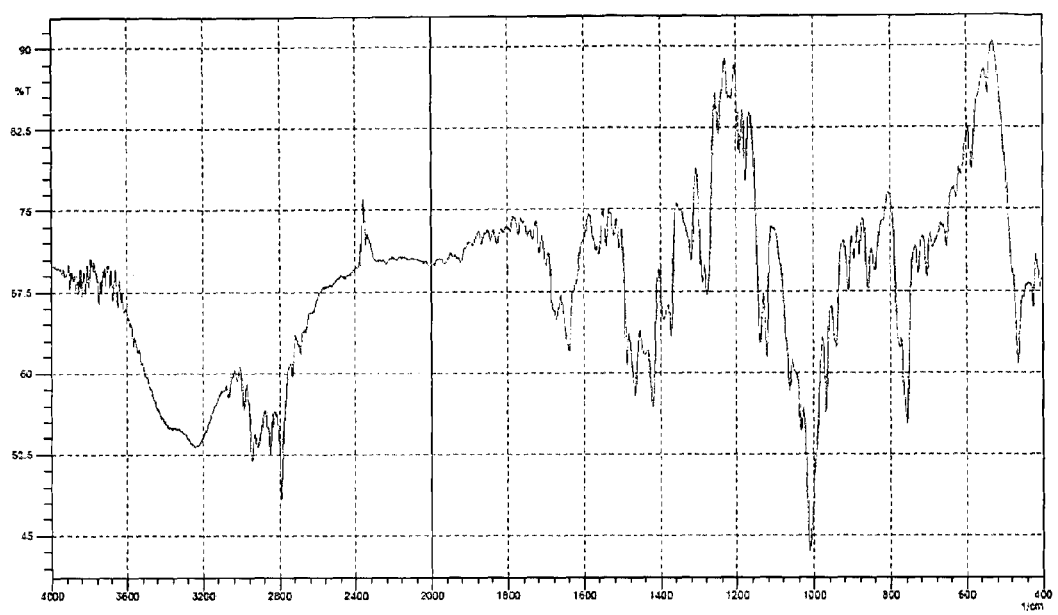
FIG. 2 depicts an infra-red spectra of a crystalline compound of structural formula VIII.

In another embodiment, the present invention relates to a crystalline compound of structural formula VIII characterized by an infra-red spectrum as depicted in FIG. 2.

In one example, the alcaftadine compound of structural formula I is prepared by reacting a compound of structural formula VIII with more than 20 moles of oxidizing reagent in an organic solvent.

In another embodiment, the present invention relates to a process of preparing alcaftadine compound of structural formula I comprising, the steps of:
 a. dissolving crude compound of structural formula VIII in an ether solvent,
 b. isolating a substantially pure compound of structural formula VIII and
 c. converting a substantially pure compound of structural formula VIII into alcaftadine compound of structural formula I.

In another embodiment, the present invention relates to a process of preparing substantially pure alcaftadine compound of structural formula I comprising reacting a compound of structural formula VIII with more than 20 moles of oxidizing reagent in an organic solvent to obtain a substantially pure alcaftadine compound of structural formula I.

The reaction of a compound of structural formula VIII with more than 20 moles of oxidizing reagent in an organic solvent can be carried out at a temperature in the range of 40° C. to 80° C. for a period of 2 hours to 24 hours.

The oxidizing reagent may be added in one lot or in several lots.

An oxidizing reagent can be selected from the group comprising, but not limited to, manganese dioxide, silver nitrate, selenium dioxide or eerie ammonium nitrate or the like or mixtures thereof.

An organic solvent according to present invention can be selected from the group comprising, but not limited to, ketones, alcohols, esters, nitriles, halogenated aliphatic hydrocarbon solvents, ethers or mixtures thereof.

The ketone solvents can be selected from the group comprising, but not limited to, acetone, methyl ethyl ketone, methyl isobutyl ketone, dibutyl ketone, diethyl ketone, dipropyl ketone, diisopropyl ketone, methyl butyl ketone, methyl propyl ketone, methyl isopropyl ketone, ethyl isopropyl ketone or mixture(s) thereof.

The alcohol solve can be selected from the group comprising, but not limited to, methanol, ethanol, propanol, isopropanol, butanol, isobutanol, t-butanol, pentanol or mixture(s) thereof.

The ester solvents can be select from the group comprising, but not limited ethyl acetate, propyl acetate, isopropyl acetate, butyl acetate, tertiary butyl acetate, pentyl acetate or mixture(s) thereof.

The nitrile solvents can be selected from the group comprising, but not limited to, acetonitrile, propionitrile or mixture(s) thereof.

The halogenated aliphatic hydrocarbon solvents can be selected from the group comprising, but not limited to, dichloromethane, dichloroethane, chloroform, carbon tetrachloride or mixture(s) thereof.

The ether solvents can be selected from the group comprising, but not limited to, tetrahydrofuran, dioxane, diethyl ether, diisopropyl ether, dibutyl ether, methyl tertiary butyl ether, methyl ethyl ether, methyl isobutyl ether or mixture(s) thereof.

The alcaftadine compound of structural formula I can be isolated by cooling the reaction mixture at a temperature in the range of 25-35° C. followed by filtering the reaction mixture to obtain a filtrate. The filtrate obtained may be washed with organic solvent and then organic layer can be separated, washed with water and dried over sodium sulphate.

The resulting organic layer containing alcaftadine compound of structural formula I may be concentrated under reduced pressure to obtain a residue of alcaftadine compound of structural formula I. The residue of alcaftadine compound of structural formula I may be crystallized by an ether solvent to obtain a substantially pure alcaftadine compound of structural formula I.

The isolated substantially pure alcaftadine compound structural formula I may be dried at a temperature in the range of 40-60° C. for a period of 2 hours to 10 hours under reduced pressure.

The term "substantially pure alcaftadine compound of structural formula I" described herein refers to an alcaftadine compound of structural formula I having less than 5% of a compound of structural formula VIII:

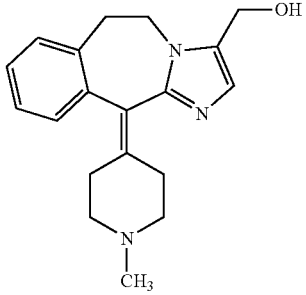

Formula VIII

EXAMPLES

In the following examples, the preferred embodiments of the present invention are described only by way of illustrating the process of the invention. However, these are not intended to limit the scope of the present invention in any way.

Example 1

Purification of a Compound of a Structural Formula VIII

A crude compound of structural formula VIII (50 grams) was dissolved in tetrahydrofuran (500 ml) at 60-65° C. and maintained for 1 hour. The resulting solution was cooled in the range of 25-35° C. to obtain a solid. The resulting solid was filtered, washed with tetrahydrofuran (50 ml) and dried, at 45-55° C. under reduced pressure for 8 hours to obtain a pure compound of structural formula VIII.
Yield: 35 grams
Purity: 99.9% (By HPLC)

Example 2

Purification of a Compound of Structural Formula VIII

A crude compound of structural formula VIII (10 grams) was dissolved in tetrahydrofuran (100 ml) at 60-65° C. and maintained for 1 hour. The resulting solution was cooled in the range of 25-35° C. to obtain a solid. The resulting solid was filtered, washed with tetrahydrofuran (10 ml) and dried at 45-55° C. under reduced pressure for 5 hours to obtain a pure compound of structural formula VIII.
Yield: 8.5 grams
Purity: 99.9% (By HPLC)

Example 3

Purification of a Compound of Structural Formula VIII

A crude compound of structural formula VIII (10 grams) was dissolved in 1,4-dioxane (100 ml) at 60-65° C. and maintained for 1 hour. The resulting solution was cooled in the range of 25-35° C. to obtain a solid. The resulting solid was filtered, washed with 1,4-dioxane (20 ml) and dried at 45-55° C. under reduced pressure for 6 hours to obtain a pure compound of structural formula VIII.
Yield: 8.7 grams
Purity: 99.8% (By HPLC)

Example 4

Preparation of a Substantially Pure Alcaftadine Compound of Structural Formula I The solution of a compound of structural formula VIII (40 grams) in chloroform (4000 ml) was added to the first lot of manganese dioxide (200 grams) at 25-35° C. and then the resulting reaction mixture was heated to 60-65° C. and stirred for 4 hours. The second lot of manganese dioxide (200 grams) was then added to the reaction mixture at 60-65° C. and stirred fix 4 hours. In this manner, third, fourth, fifth and sixth lots of manganese dioxide (200 grams) were respectively added to the reaction mixture at 60-65° C. and after each lot addition, the reaction mixture was stirred for 4 hours. The resulting reaction mixture was cooled to 25-35° C., filtered and washed with chloroform (1000 ml). The resulting organic layer was washed with water (2×400 ml), dried over sodium sulphate (200 grams) and concentrated under reduced pressure to obtain a residue. Diethyl ether (150 ml) was added to the resulting residue and then stirred for 2 hours at 25-35° C. to obtain a suspension. The resulting suspension was filtered, washed with diethyl ether (50 ml) and dried under reduced pressure at 45-55° C. for 8 hours to obtain a substantially pure alcaftadine compound of structural formula I.
Yield: 30 grams
Purity: 98.7% (By HPLC)

Example 5

Preparation of a Substantially Pure Alcaftadine Compound of Structural Formula I The solution of a compound of structural formula VIII (20 grams) in chloroform (2000 ml) was added to manganese dioxide (600 grams) at 25-35° C. and then the resulting reaction mixture was heated to 60-65° C. and stirred for 18 hours. The resulting reaction mixture was cooled to 25-35° C., filtered and washed with chloroform (500 ml). The resulting organic layer was washed with water (2×200 ml), dried over sodium sulphate (100 grams) and concentrated under reduced pressure to obtain a residue. Diethyl ether (100 ml) was added to the resulting residue and then stirred for 1 hour at 25-35° C. to obtain a suspension. The resulting suspension was filtered, washed with diethyl ether (25 ml) and dried under reduced pressure at 45-55° C. for 6 hours to obtain a substantially pure alcaftadine compound of structural formula I.
Yield: 15 grams
Purity: 98.8% (By HPLC)

Example 6

Preparation of a Substantially Pure Alcaftadine Compound of Structural Formula I The solution of a compound of structural formula VIII (40 grams) in chloroform (4000 ml), was added to manganese dioxide (1200 grams) at 25-35° C. and then the resulting reaction mixture was heated to 60-65° C. and stirred for 16 hours. The resulting reaction mixture was cooled to 25-35° C., filtered and washed with chloroform (1000 ml). The resulting organic layer was washed with water (2×400 ml), dried over sodium sulphate (200 grams) and concentrated under reduced pressure to obtain a residue. Diethyl ether (200 ml) was added to the resulting residue and then stirred for 1 hour at 25-35° C. to obtain a suspension. The resulting suspension was filtered, washed with diethyl ether (50 ml) and dried under reduced pressure at 45-55° C. for 8 hours to obtain a substantially pure alcaftadine compound of structural formula I.

Yield: 30 grams
Purity: 98.9% (By HPLC)

The scope of the claims should not be limited by the preferred embodiments and examples described herein, but should be given the broadest interpretation consistent with the written description as a whole.

The invention claimed is:
1. A process of purification of compound of structural formula VIII comprising the steps of:
   a) dissolving a crude compound of structural formula VIII in a tetrahydrofuran solvent, the crude compound having more than 15% of a compound of structural formula XIV; and
   b) isolating a substantially pure compound of structural formula VIII having the formula:

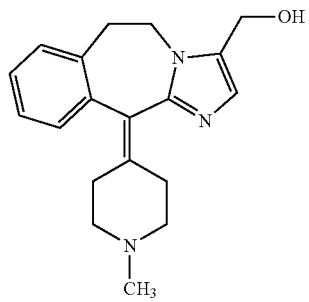

Formula VIII wherein the compound of structural formula XIV has the formula:

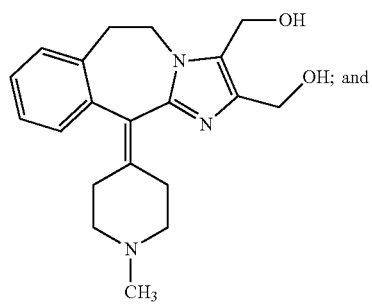

Formula XIV the substantially pure compound of structural formula VIII has less than 15% of the compound of structural formula XIV.

2. The process according to claim 1, wherein the crude compound of structural formula VIII is dissolved at a temperature in the range of 40° C. to 80° C., maintained for 30 minutes to 2 hours, and then cooled in the range of 20° C. to 30<C. to obtain the substantially pure compound of structural formula VIII.

3. The process according to claim 1, wherein the substantially pure compound of structural formula VIII is isolated by the steps of filtration, centrifugation, washing, drying or combinations thereof.

4. The process according to claim 3, wherein the isolated substantially pure compound of structural formula VIII is dried at a temperature in the range of 40° C. to 80° C. for a period of 2 hours to 12 hours under reduced pressure.

5. A tetrahydrofuran solvated compound of structural formula XVI having the formula:

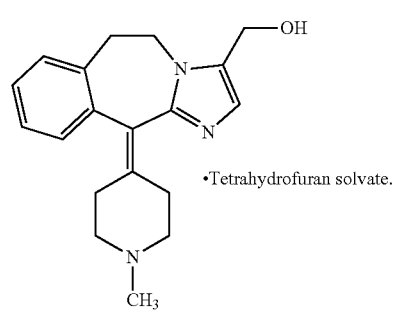

Formula XVI

·Tetrahydrofuran solvate.

6. A process of preparing an alcaftadine compound of structural formula I comprising the steps of:
   a) dissolving a crude compound of structural formula VIII in a tetrahydrofuran solvent;
   b) isolating a substantially pure compound of structural formula VIII; and
   c) converting the substantially pure compound of structural formula VIII into an alcaftadine compound of structural formula I having the formula:

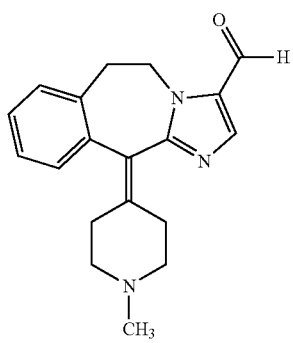

Formula I wherein the crude compound of structural formula VIII has more than 15% of a compound of structural formula XIV and has the formula:

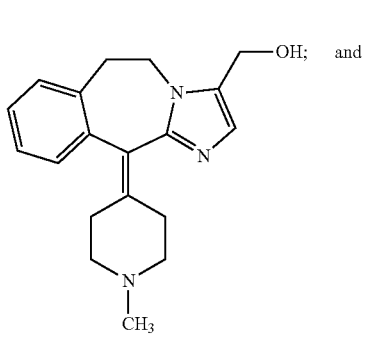

Formula VIII and the compound of structural formula XIV has the formula:
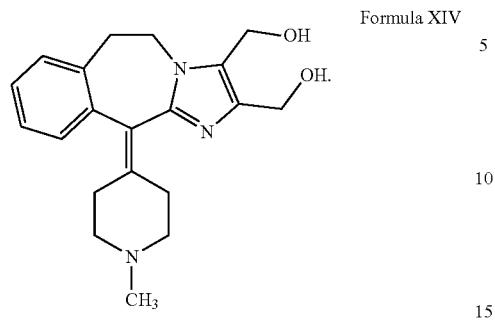
Formula XIV
* * * * *

UNITED STATES PATENT AND TRADEMARK OFFICE
CERTIFICATE OF CORRECTION

PATENT NO. : 9,255,105 B2
APPLICATION NO. : 14/391465
DATED : February 9, 2016
INVENTOR(S) : Bobba Venkata et al.

Page 1 of 1

It is certified that error appears in the above-identified patent and that said Letters Patent is hereby corrected as shown below:

In the Specification

Col 11, line 11, "VIII may be isolated by any known process in the at such as" should read --VIII may be isolated by any known process in the art such as--

Col 11, line 17, "for a period of 2 horns to 12 hours under reduced pressure." should read --for a period of 2 hours to 12 hours under reduced pressure.--

Col 11, line 24, "One example of a solvated a compound of structural for" should read --One example of a solvated compound of structural for--

Col 12, line 31, "The alcohol solve can be selected from the group comprising" should read --The alcohol solvent can be selected from the group comprising--

Col 12, line 35, "The ester solvents can be select from the group comprising," should read --The ester solvents can be selected from the group comprising,--

Col 14, line 20, "stirred fix 4 hours. In this manner, third, fourth, fifth and sixth" should read --stirred for 4 hours. In this manner, third, fourth, fifth and sixth--

In the Claims
Col 15, line 66, "30< C. to obtain the substantially pure compound of structural" should read --30° C. to obtain the substantially pure compound of structural--

Signed and Sealed this
Twenty-sixth Day of July, 2016

Michelle K. Lee
*Director of the United States Patent and Trademark Office*